United States Patent
Song et al.

(10) Patent No.: US 11,576,655 B2
(45) Date of Patent: Feb. 14, 2023

(54) METHOD FOR HARMONIC SHEAR WAVE DETECTION WITH A LOW FRAME RATE ULTRASOUND SYSTEM

(71) Applicant: Mayo Foundation for Medical Education and Research, Rochester, MN (US)

(72) Inventors: Pengfei Song, Champaign, IL (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 201 days.

(21) Appl. No.: 16/764,150

(22) PCT Filed: Nov. 14, 2018

(86) PCT No.: PCT/US2018/060901
§ 371 (c)(1),
(2) Date: May 14, 2020

(87) PCT Pub. No.: WO2019/099439
PCT Pub. Date: May 23, 2019

(65) Prior Publication Data
US 2020/0275913 A1    Sep. 3, 2020

Related U.S. Application Data

(60) Provisional application No. 62/586,359, filed on Nov. 15, 2017.

(51) Int. Cl.
*A61B 8/08*   (2006.01)
*G01S 7/52*   (2006.01)

(52) U.S. Cl.
CPC .............. *A61B 8/485* (2013.01); *A61B 8/483* (2013.01); *A61B 8/5276* (2013.01);
(Continued)

(58) Field of Classification Search
CPC .... A61B 8/485; A61B 8/5276; G01S 7/52077
See application file for complete search history.

(56) References Cited

U.S. PATENT DOCUMENTS

| 8,668,647 B2 | 3/2014 | Eskandari |
| 2005/0165306 A1* | 7/2005 | Zheng ................... A61B 8/485 600/437 |

(Continued)

FOREIGN PATENT DOCUMENTS

| EP | 2889004 A1 | 7/2015 |
| WO | 2016069750 A1 | 5/2016 |
| WO | 2017062553 A1 | 4/2017 |

OTHER PUBLICATIONS

Eskandari, H., et al. "Bandpass sampling of high-frequency tissue motion." Proceedings of the Ninth International Conference on the Ultrasonic Measurement and Imaging of Tissue Elasticity. Snowbird, Utah, USA. Oct. 2010.

(Continued)

*Primary Examiner* — Amanda Lauritzen Moher
*Assistant Examiner* — Brooke Lyn Klein
(74) *Attorney, Agent, or Firm* — Quarles & Brady LLP

(57) ABSTRACT

Systems and methods for harmonic shear wave detection using low frame rate ultrasound, or a three-dimensional (3D) volumetric scan, are provided. As one example, spurious motion sources, such as intrinsic tissue motion and waves that are not at the incident wave harmonic frequency, are removed based on a scanning sequence in which repeated acquisitions from a given subvolume occur closely in time so as to render effects of the spurious motions negligible. As another example, sampling frequency and center frequency are selected such that the spurious motion signal spectra do not overlap with aliased shear wave motion spectra, such that the spurious motions can be filtered.

6 Claims, 10 Drawing Sheets

(52) U.S. Cl.
CPC ...... *G01S 7/52042* (2013.01); *G01S 7/52077* (2013.01); *G01S 7/52085* (2013.01)

(56) References Cited

U.S. PATENT DOCUMENTS

| | | | | |
|---|---|---|---|---|
| 2013/0123630 A1* | 5/2013 | Freiburger | ............. | A61B 8/485 600/443 |
| 2015/0272547 A1* | 10/2015 | Freiburger | ............... | A61B 8/52 600/438 |
| 2018/0296191 A1 | 10/2018 | Mellema | | |

OTHER PUBLICATIONS

International Searching Authority, International Search Report and Written Opinion for application PCT/US2018/060901, dated Apr. 25, 2019.

Song, P., et al. "Two-dimensional shear-wave elastography on conventional ultrasound scanners with time-aligned sequential tracking (TAST) and comb-push ultrasound shear elastography (CUSE)." IEEE transactions on ultrasonics, ferroelectrics, and frequency control 62.2 (2015): 290-302.

Waters and Jarrett, "Bandpass signal sampling and coherent detection," in IEEE Transactions on Aerospace and Electronic Systems, vol. AES-18, No. 6, pp. 731-736, Nov. 1982.

* cited by examiner

METHOD FOR HARMONIC SHEAR WAVE DETECTION WITH A LOW FRAME RATE ULTRASOUND SYSTEM

CROSS-REFERENCE TO RELATED APPLICATIONS

This application is a 371 U.S. National Phase application of PCT/US2018/060901, filed Nov. 14, 2018, which claims the benefit of U.S. Provisional Patent Application Ser. No. 62/586,359, filed on Nov. 15, 2017, and entitled "METHOD FOR HARMONIC SHEAR WAVE DETECTION WITH A LOW FRAME RATE ULTRASOUND SYSTEM," which is herein incorporated by reference in its entirety.

STATEMENT REGARDING FEDERALLY SPONSORED RESEARCH

This invention was made with government support under DK106957 awarded by the National Institutes of Health. The government has certain rights in the invention.

BACKGROUND

Harmonic ultrasound shear wave elastography utilizes cyclic harmonic shear waves to estimate tissue mechanical properties such as tissue stiffness. One example of harmonic shear wave elastography is to use an external mechanical shaker that vibrates at a certain harmonic frequency to introduce shear waves into the tissue. This method has better imaging penetration than acoustic radiation force-based shear wave elastography, and is also easier to implement on low frame-rate ultrasound scanners (e.g., conventional ultrasound systems with line-by-line scanning) or in three-dimensional (3D) shear wave imaging.

When the imaging frame rate is lower than the Nyquist frequency of shear wave, the detected shear wave signal will be aliased. However, because of the cyclic nature of the sinusoidal harmonic shear wave signal (i.e., the tissue particle is always at the same position at the same phase over different cycles), the aliasing artifact can be corrected and removed by phase-shifting shear wave signals detected at different vibration cycles to reconstruct a non-aliased shear wave signal, as described in co-pending International Appln. No. PCT/US2016/055649.

In practice, harmonic shear wave propagation in tissue is typically accompanied by intrinsic physiologic motion of the tissue or other waves with different and often unknown frequencies than that of the harmonic shear wave. As a result, the combined wave motion is not monochromatic anymore, which violates the assumption of cyclic waves when using the phase-shifting detection approach described in co-pending International Appln. No. PCT/US2016/055649.

Thus, there remains a need to robustly remove the intrinsic tissue motion and the waves that are not at the incident wave harmonic frequency when detecting harmonic shear waves using a low frame-rate scanner or using 3D volumetric scan.

SUMMARY OF THE DISCLOSURE

The present disclosure addresses the aforementioned drawbacks by providing a method for producing an image from data acquired using an ultrasound system. Shear wave data are acquired with an ultrasound system having an ultrasound transducer by operating the ultrasound system according to a scanning sequence in which the shear wave data are acquired from each of a plurality of subvolumes. Each subvolume is associated with a subset of transducer elements in the ultrasound transducer. The shear wave data are sequentially acquired from the plurality of subvolumes such that shear wave data are acquired from each subvolume at least twice in repeated succession. The time interval between repeated acquisitions from a same subvolume is sufficiently short such that background motion in that subvolume is negligible between the repeated acquisitions. An image is then generated from the shear wave data. Errors attributable to the background motion are reduced in the image.

It is another aspect of the present disclosure to provide a method for producing an image from shear wave data acquired from a subject using an ultrasound system. An estimate of tissue motion in the subject is provided to a computer system. A sampling frequency and a center frequency are selected based on the estimate of the tissue motion in the subject, such that aliased shear wave signals are positioned in a frequency domain so as not to overlap with frequency bins corresponding to the tissue in the subject. Shear wave data are acquired using an ultrasound system that is operated to acquire the shear wave data from a subject using the selected sampling frequency and center frequency while harmonic shear waves are induced in the subject. Filtered shear wave data are generated by filtering the shear wave data to remove data corresponding to the tissue motion. An image of the subject is produced from the filtered shear wave data. Errors attributable to the background motion are reduced in the image.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for harmonic shear wave detection using low frame rate ultrasound or a three-dimensional (3D) volumetric scan. In particular the systems and methods described in the present disclosure remove intrinsic tissue motion and waves that are not at the incident wave harmonic frequency are removed when detecting the harmonic shear waves using a low frame-rate scanner or a 3D volumetric scan. As one example, a low-frame rate or low-volume rate can correspond to a frame rate or scan rate that does not satisfy the Nyquist sampling criterion. For instance, a low frame rate or a low scan rate may be present where the sampling frequency is less than twice the shear wave frequency.

Figure 1:
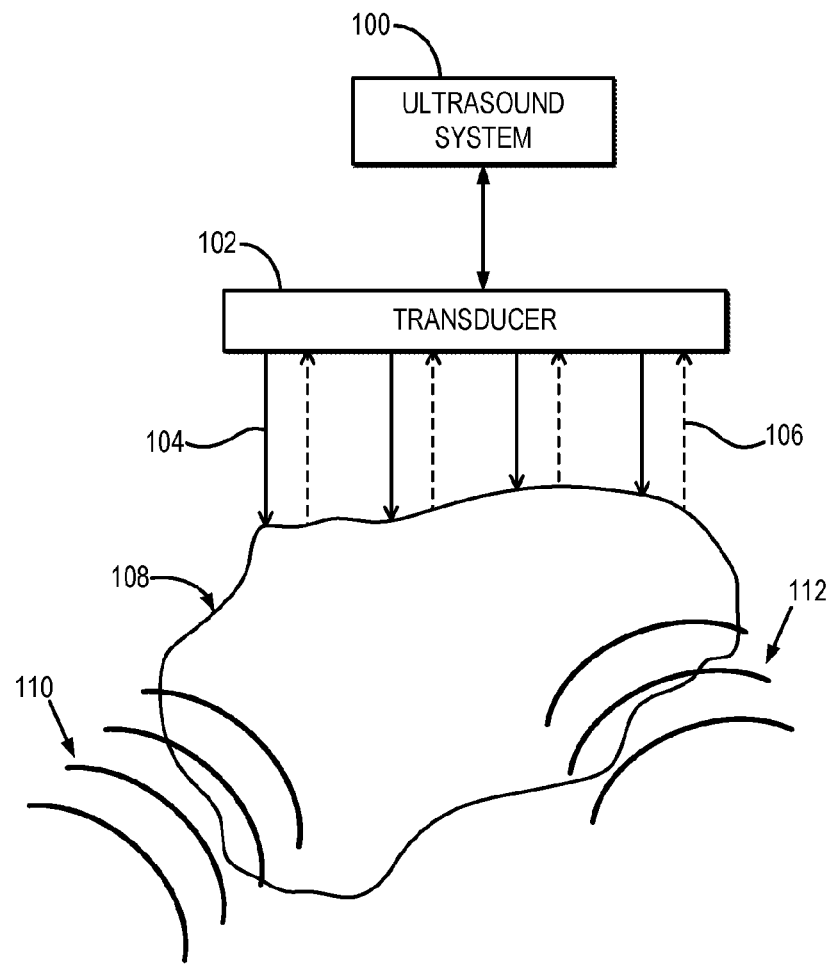
FIG. 1 is a block diagram of an example ultrasound system that can implement the methods described in the present disclosure.

Referring to FIG. 1, an example of an ultrasound system 100 that can implement the methods for harmonic shear wave motion detection descried in the present disclosure is shown. The ultrasound system 100 may be, for example, a pulse-echo mode ultrasound system. The ultrasound system 100 drives an ultrasound transducer 102 to transmit ultrasound waves 104 into a region-of-interest, such as a targeted tissue 108, and receives ultrasound waves 106 from the same targeted tissue 108. Harmonic shear waves 110 and 112 are introduced into the targeted tissue 108. As one example, the harmonic shear waves 110 and 112 can be generated by external vibrations (e.g., vibrators, loudspeakers, a vibration bed, a vibration cushion, a vibrating chair). As another example, the harmonic shear waves 110 and 112 can be generated by physiological motions (e.g., humming). As yet another example, the harmonic shear waves 110 and 112 can be generated by an acoustic radiation force (e.g., a series of cyclic push pulses applied by the ultrasound transducer 102).

The ultrasound transducer 102 can be a one-dimensional (1D) array transducer for two-dimensional (2D) shear wave imaging, a 1D transducer with mechanical sweep for 3D shear wave imaging, a 1.5D transducer for 3D shear wave imaging, a true 2D array transducer for 3D shear wave imaging, or so on. The imaging frame rate in 2D imaging or volume rate in 3D imaging can be controlled by the ultrasound system 100. The ultrasound system 100 can be capable of performing a line-by-line or a zone-by-zone (one zone contains multiple lines) scanning mode in 2D imaging, and a volume-by-volume scanning mode in 3D imaging. The ultrasound system 100 can also be capable of producing radiofrequency ultrasound data, in-phase quadrature (IQ) ultrasound data, or so on. The ultrasound system 100 can detect one or more shear wave signals at one time instant for each interrogated tissue location.

After the shear wave motion has been estimated using the methods described in the present disclosure, the ultrasound system or another computer system can be operated to generate images, compute quantitative parameters, or both. For instance, mechanical properties can be computed from the estimated shear wave signals, and images of these properties can be generated.

Figure 2:
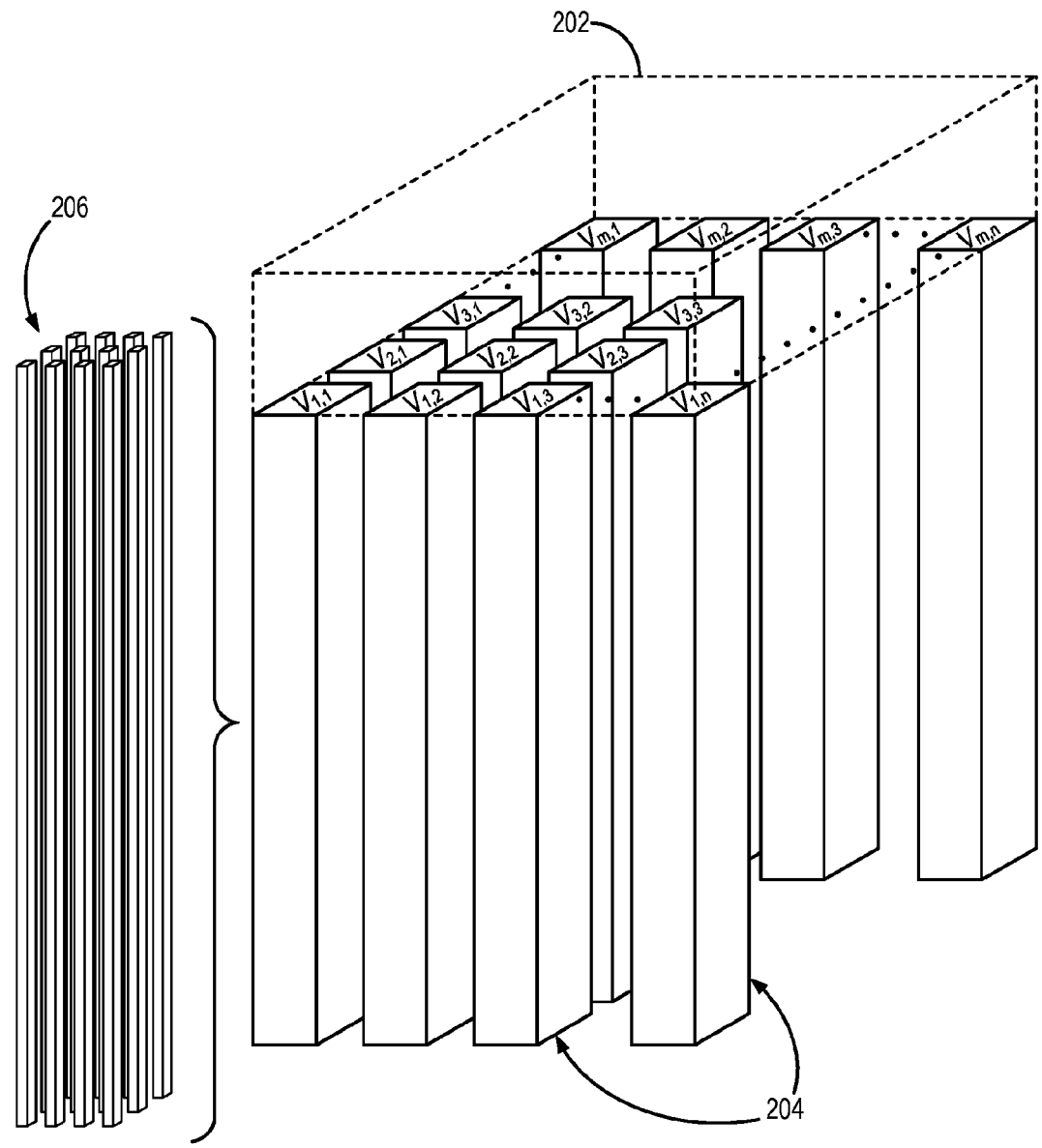
FIG. 2 illustrates an example ultrasound transducer being used to acquire data over a number of different subvolumes.

FIG. 2 illustrates an example of a scanning sequence that can be used for harmonic shear wave detection. In this example, a 3D harmonic shear wave detection sequence with a 2D array transducer is depicted. The same principles can be applied to 2D shear wave detection with a 1D array transducer, or 3D shear wave detection with a 1D array transducer with mechanical sweep or a 1.5D or 2D array transducer.

In this example, a 2D array transducer 202 that includes at least two transducer elements along the elevational direction of the transducer 202 is used for volumetric imaging. The scanning subvolumes 204 are indexed as $V_{1,1}$, $V_{1,2}$, $V_{1,3}$, ..., $V_{2,1}$, $V_{2,2}$, ..., $V_{m,n}$, where the first subscript number indicates the index of the rows of each scanning subvolume 204, and the second subscript number indicates the index of the columns of each scanning subvolume 204. The total number of scanning subvolumes 204 is m×n (i.e., the entire scanning volume contains of m×n scanning subvolumes, with the index m corresponding to the elevational direction of the scanning volume, and the index n corresponding to the lateral direction of the scanning volume). Within each subvolume 204, there is at least one scanning A-line 206 that can be parallel beamformed during a single pulse-echo cycle.

The ultrasound system unit 100 can program the transmit and receive sequence of the scanning subvolumes 204 in a desired order. Listed below are two examples of scanning sequences that can be used for harmonic shear wave detection:

Example Scanning Sequence 1

$$\{V_{1,1} \to V_{1,2} \to \ldots \to V_{1,n} \to V_{2,1} \to \ldots \to V_{2,n} V_{m,1} \to \ldots \to V_{m,n}\}_R$$

where the subscript R indicates that the sequence within the brackets is repeated R times.

Example Scanning Sequence 2

$$\{V_{1,1} \to V_{1,2} \to \ldots \to V_{1,n}\}_R \{V_{2,1} \to V_{2,2} \to \ldots \to V_{2,n}\}_R \{V_{m,1} \to V_{m,2} \to \ldots \to V_{m,n}\}_R$$

The subvolumes 204 with consecutive indices (e.g., $V_{1,1}$ and $V_{1,2}$) can be spatially adjacent subvolumnes 204 or non-spatially adjacent subvolumes 204. Similar sequences can be easily translated to 2D imaging for shear wave detection with a 1D array transducer, or 3D imaging for shear wave detection with a 1D array transducer with mechanical sweep or a 1.5D array transducer. In the case of a 2D imaging with a 1D array transducer, the above sequences can be modified to m=1.

The scanning frame rate or volume rate for shear wave detection is defined by the inverse of the total scanning time of one frame or one volume (i.e., the total scanning time of all the subvolumes 204 within each bracket in the scanning sequences listed above), and can be indicated as $f_s$. The pulse-repetition-frequency, $f_{PRF}$, of the ultrasound system 100 is defined by the inverse of the time interval between two consecutive subvolume 204 scans (i.e., the time interval between $V_{1,1}$ and $V_{1,2}$ as in scanning sequence 1). The pulse-repetition-frequency, $f_{PRF}$, is typically determined by the speed of the ultrasound propagation. The relationship between $f_s$ and $f_{PRF}$ of the above example scanning sequences is:

$$f_s = \frac{f_{PRF}}{mn + t_c f_{PRF}}; \quad (1)$$

for scanning sequence 1, where $t_c$ is a constant time inserted to the end of the scanning of each frame or volume (e.g., to the end of the last subvolume transmission within each bracket) to satisfy a certain $f_s$, m is the number of elevational scanning subvolumes, and n is the number of lateral scanning volumes. For scanning sequence 2, the relationship is, $$f_s = \frac{f_{PRF} I}{mn + t_c f_{PRF} I}; \quad (2)$$

where $t_c$ is a constant time inserted to the end of each subgroup of subvolumes (e.g., to the end of the last subvolume transmission within each bracket), I is the number of subvolumes within each subgroup of subvolumes (e.g., the number of subvolumes from $V_{1,1}$ to $V_{1,n}$ as in scanning sequence 2, in which case I is equal to n) that are being repeatedly and sequentially transmitted. Scanning sequence 2 provides faster scanning frame rate or volume rate than scanning sequence 1.

Figure 3:
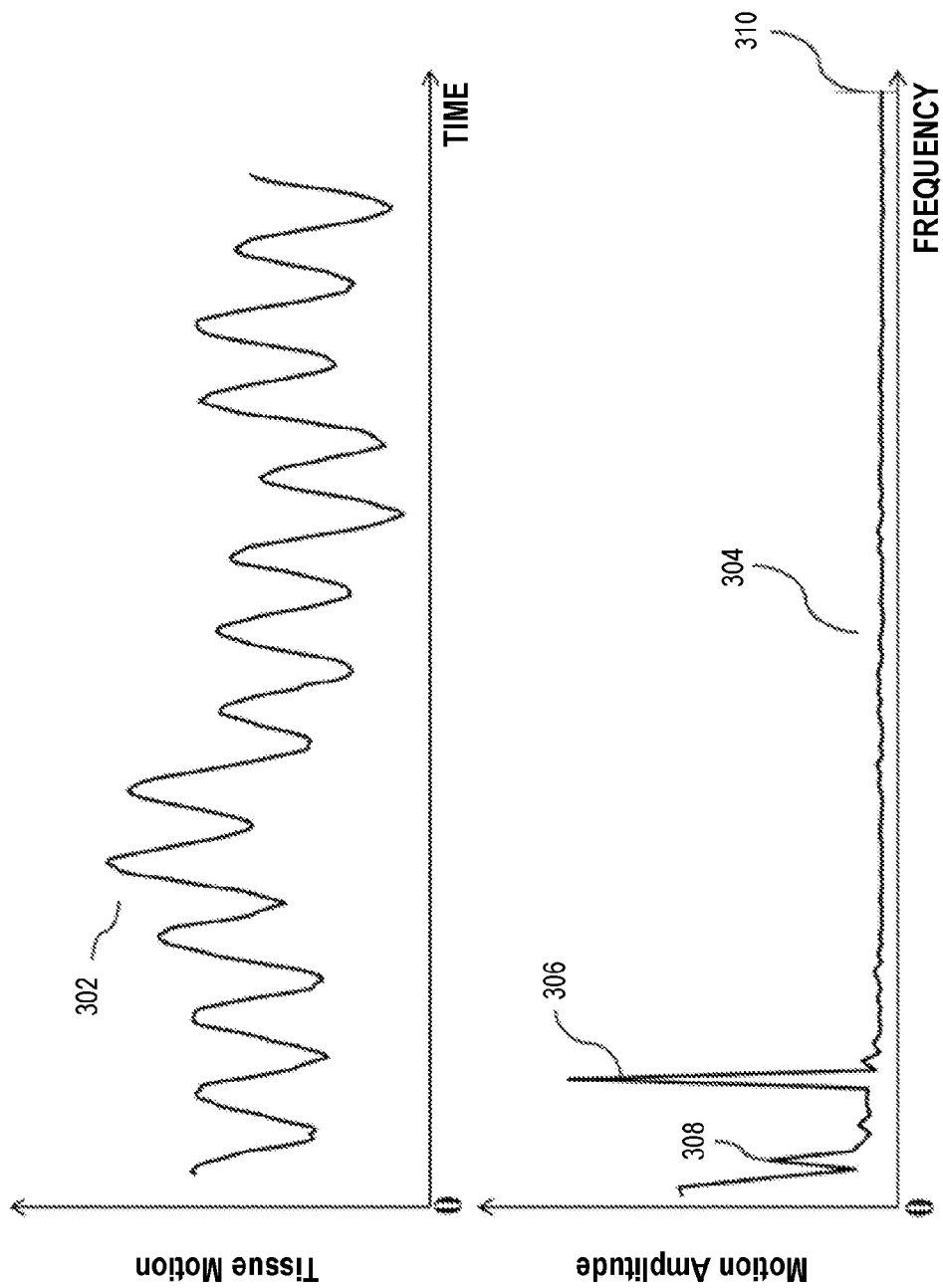
FIG. 3 shows an example shear wave motion signal that is corrupted by tissue motion and a corresponding frequency spectrum.

The goal of the above mentioned scanning sequence examples and all the other shear wave detection sequences with the described ultrasound system 100 is to robustly detect shear wave motion within the targeted tissue 108. FIG. 3 illustrates an example of a shear wave motion signal 302, from which the cyclic and fast-oscillating shear wave motion can be seen as riding on top of an underlying tissue motion (e.g., intrinsic physiologic tissue motion or other tissue motions with different frequencies than the applied shear wave frequency). The frequency spectrum 304 of the shear wave motion signal 302 is also shown. In the frequency spectrum 304, the shear wave signal that appears at a certain frequency $f_0$ (e.g., the external vibration frequency) is shown as peak 306; the underlying tissue motion with a center frequency of $f_t$ is shown as peak 308; and the Nyquist frequency, $f_N$, for shear wave detection, which is equal to half the sampling frequency (e.g., $f_s$) is indicated at 310.

If the Nyquist frequency, $f_N$, is greater than the shear wave frequency, $f_0$, then a highpass filter or a bandpass filter with a low cutoff frequency that is higher than the underlying tissue motion frequency, $f_t$, can be applied to remove the underlying tissue motion and extract the shear wave motion. However, when the Nyquist frequency, $f_N$, is smaller than or equal to the shear wave frequency, $f_0$ (which frequently happens when detecting shear waves with a low frame-rate or low volume-rate scan), aliasing will occur and the shear wave signal 306 will appear at an aliased frequency, $f_a$, location on the frequency spectrum with, $f_a = |K f_s - f_0|$, where K=0, ±1, ±2, . . . .

If $f_a$ is overlapped with the tissue frequency, $f_t$ (e.g., is the shear wave signal peak 306 is aliased to frequency bins that are overlapped with the tissue motion peak 308), then the shear wave signal becomes inseparable from the underlying tissue motion and consequently cannot be detected. As a result, the shear wave aliasing-correction approaches will not work.

Methods for removing the underlying tissue motion when aliasing occurs, such that the targeted shear wave signal can be robustly detected, are now described below.

Figure 4:
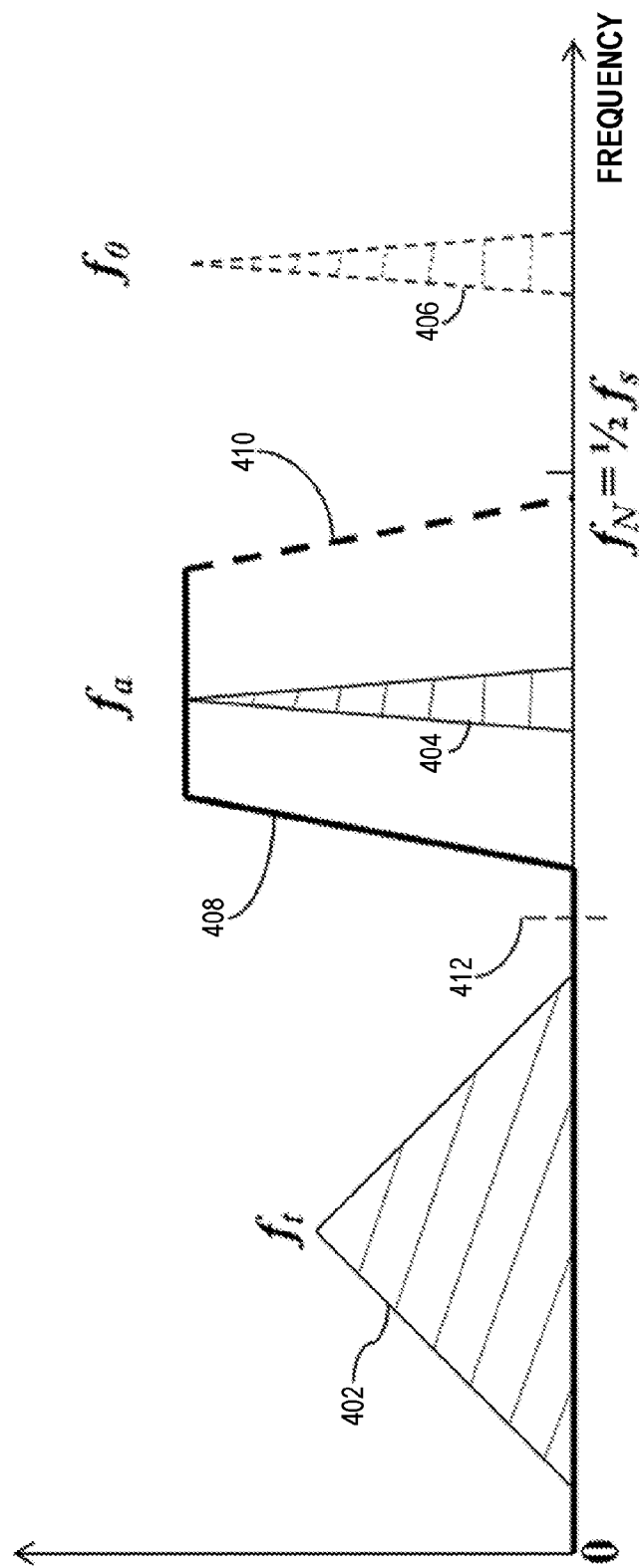
FIG. 4 depicts the separation of tissue motion spectral data from aliased and non-aliased shear wave spectral data, such that the tissue motion spectral data can be filtered and removed.

Referring first to FIG. 4, one example method for removing the underlying tissue motion is illustrated. As mentioned above, when aliasing occurs, the aliased frequency, $f_a$, (shown as signal peak 404) is equal to $f_a = |K f_s - f_0|$, with K=0, ±1, ±2, . . . . Therefore, by carefully choosing the sampling frequency, $f_s$, and the shear wave frequency, $f_0$, (shown as signal peak 406), the aliased frequency component 404 can be positioned on the frequency spectrum so that it is not overlapped with the underlying tissue motion frequency, $f_t$ (shown as signal peak 402), as shown in FIG. 4. By establishing this relationship between the relevant frequencies, a highpass filter (e.g., filter 408) or a bandpass filter (e.g., filter 410) can be used to remove the underlying tissue motion from the aliased frequency spectrum.

In practice, an estimate of the underlying tissue motion spectrum can be obtained by executing a shear wave detection sequence without the shear wave signal (e.g., with the vibration source turned off), and performing a Fourier analysis of the detected motion signal to determine the underlying tissue motion spectrum and an upper frequency limit 412. To ensure that the underlying tissue motion signal is not aliased, a higher scan frame rate or volume rate can be used by reducing the size of the frame or the volume. Then, $f_s$, $f_0$, or both can be chosen such that $f_a$ is not overlapped with $f_t$.

Figure 5:
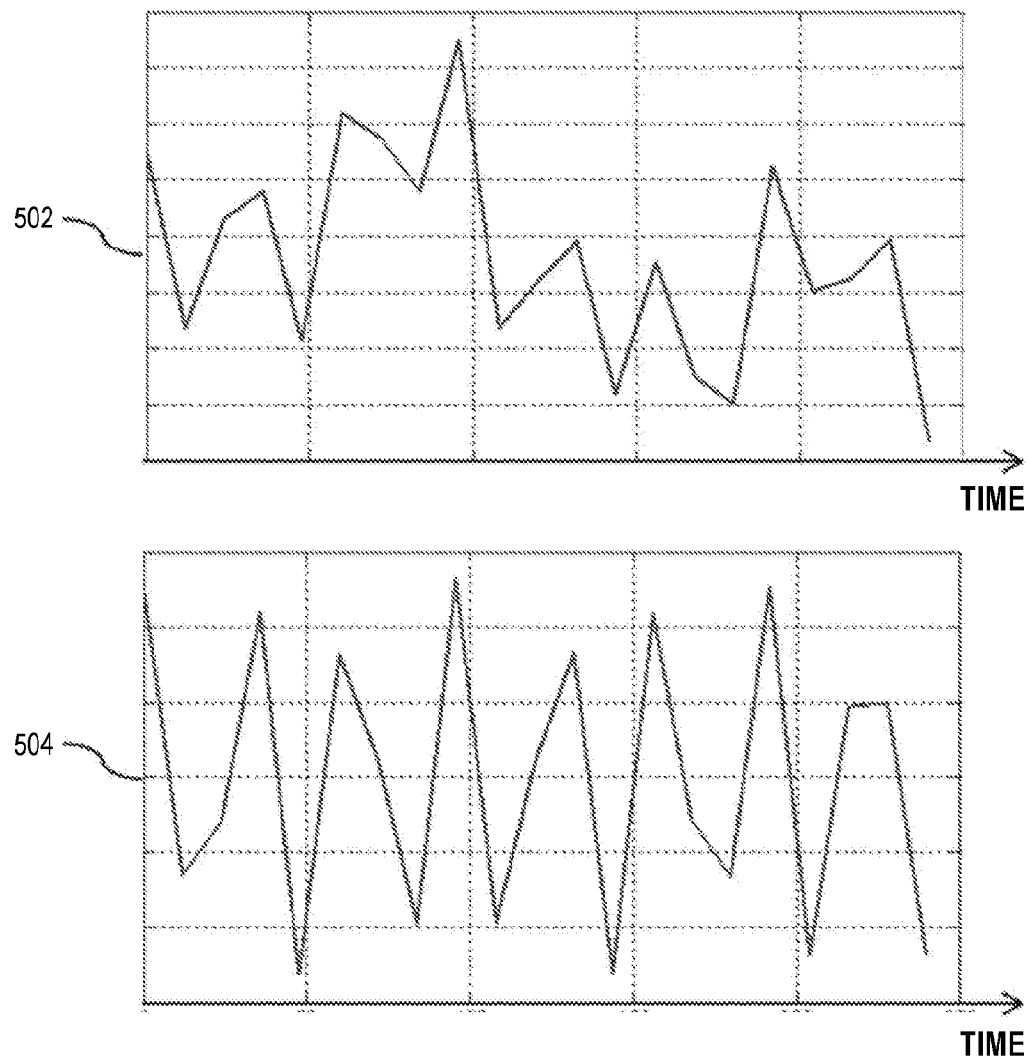
FIG. 5 illustrates an example shear wave motion signal before and after filtering according to the techniques illustrated in FIG. 4.

FIG. 5 shows an example result of using this method. In this example, the upper frequency limit of the underlying tissue motion was determined as 15 Hz. A sampling frequency, $f_s$, of 90 Hz and a shear wave frequency, $f_0$, of 60 Hz were chosen to position the aliased shear wave frequency, $f_a$, at 30 Hz. The signal plot 502 shows the detected aliased shear wave signal riding on top of the underlying tissue motion signal. After highpass filtering using a filter with a low cutoff frequency of 20 Hz, the underlying tissue motion was removed and the remaining signal contained the aliased shear wave signal, as shown in signal plot 504.

In addition to the requirement of positioning the aliased shear wave frequency to a frequency location that is not overlapped with the underlying tissue motion, the sampling frequency $f_s$ and shear wave frequency $f_0$ can also be selected to satisfy the criterion that within a certain amount of time, T, different phases of a shear wave cycle can be sampled so that a non-aliased shear wave signal can be reconstructed using an aliasing-correction approach, such as the phase-shifting method described in co-pending International Appln. No. PCT/US2016/055649, which is herein incorporated by reference in its entirety. The time, T, can be smaller than 5 seconds so that a breath-hold can be performed during shear wave detection to minimize physiologic motion. At a given sampling frequency, $f_s$, a scanning time, T, provides N temporal shear wave samples, $N=T f_s - 1$. The shear wave phase, $\phi_{sw}$, of these N shear wave samples is given by, $$\phi_{sw}(i) = 2\pi f_0 \frac{i}{f_s}, \text{ for } i = 1, 2, \ldots, N. \quad (3)$$

Figure 6:
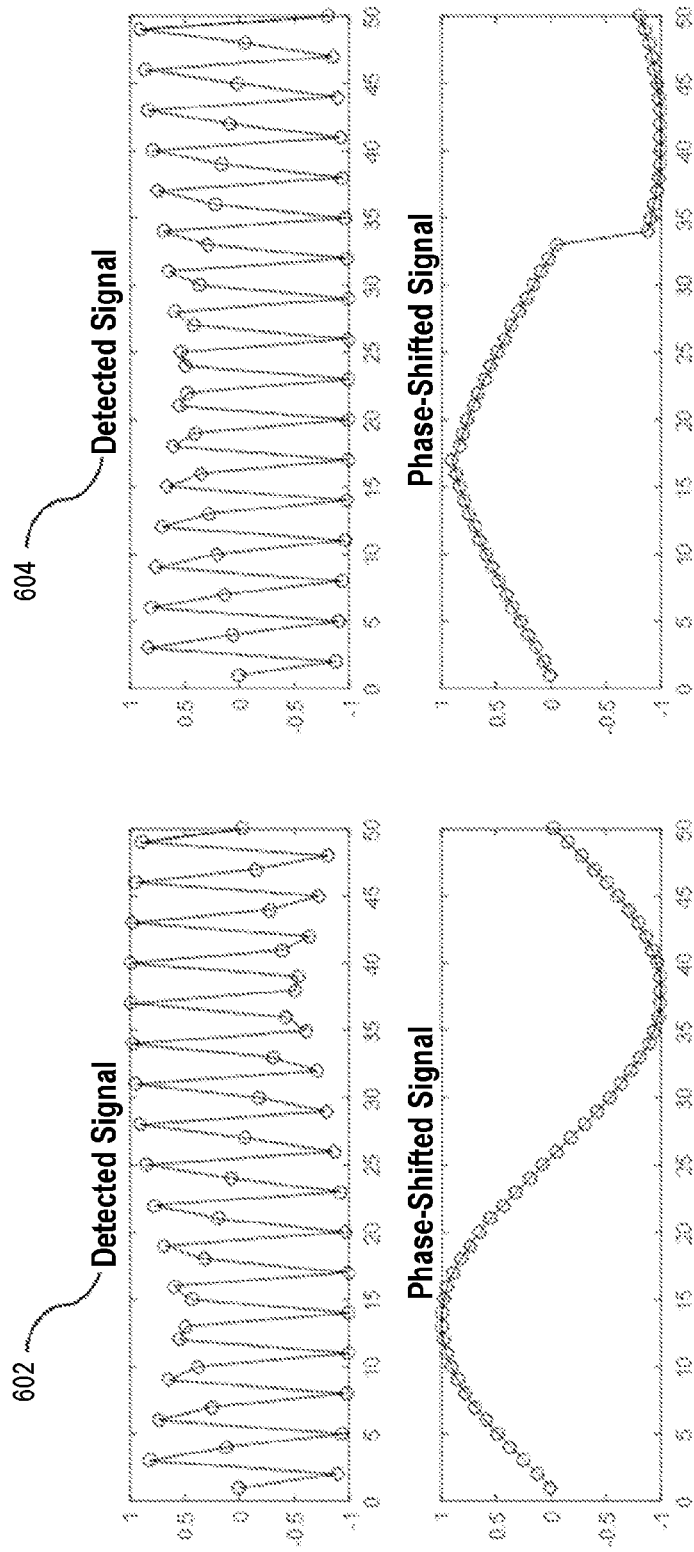
FIG. 6 depicts examples of detected shear wave signals before and after phase shifting, where the sampling frequency used to acquire the signals on the left was selected to evenly distribute the shear wave signal across the full shear wave cycle and the sampling frequency used to acquire the signals on the right was not selected in this manner.

Using the shear wave phase information from Eqn. (3), the detected shear wave signal can be predicted, and the sampling frequency, $f_s$, and shear wave frequency, $f_0$, can be selected so that a full shear wave cycle can be sampled as evenly as possible with N+1 detection frames. For example, with 51 detection frames (corresponding to 50 temporal shear wave samples), if the shear wave frequency is 60 Hz, a sampling frequency of 89.1 Hz can be selected to achieve an even sampling of the full shear wave cycle, as shown by signals plots 602 in FIG. 6. The lower panel of the phase-shifted signal in signal plots 602 is given by, (4);

$$\phi_{phase-shifted}(j) = \mathbb{S}\{\text{mod}(\phi_{sw}(i), 2\pi)\}, \text{for } i=1, 2, \ldots, N \quad (4);$$

where "mod" is calculating the remainder of the detected shear wave phase and $2\pi$; $\mathbb{S}$ is the sorting operation that sorts the remainder phase in an ascending order; and j is the new index of the sorted and phase-shifted signal.

After phase-shifting, the detected shear wave signals are evenly distributed across the full shear wave cycle. When choosing a sampling frequency of 89.5 Hz, as shown by signal plots 604 in FIG. 6, however, the detected shear wave signal mostly concentrates in the first half of the shear wave cycle. Different methods can be designed to determine an optimal combination of $f_s$ and $f_0$ to achieve evenly-distributed sampling phases. As one example, the following minimization problem can be used:

$$\operatorname*{argmin}_{f_s, f_0}\left\{\left|\phi_d(f_s, f_0) - 2\pi\frac{i-1}{N}\right|\right\}, \text{ for } i = 1, 2, \ldots, N; \quad (5)$$

where $\phi_d$ is the phase of the detected shear wave signal after phase-shifting (e.g., the lower panels in FIG. 6), and the second term inside the minimization equation is the ideal evenly-distributed phase across N samples.

After the optimal configurations of sampling frequency and shear wave frequency have been determined, which satisfies both the aliasing frequency position requirement and the even phase distribution requirement, the shear wave detection sequence can be executed to obtain the shear wave signal.

Figure 7:
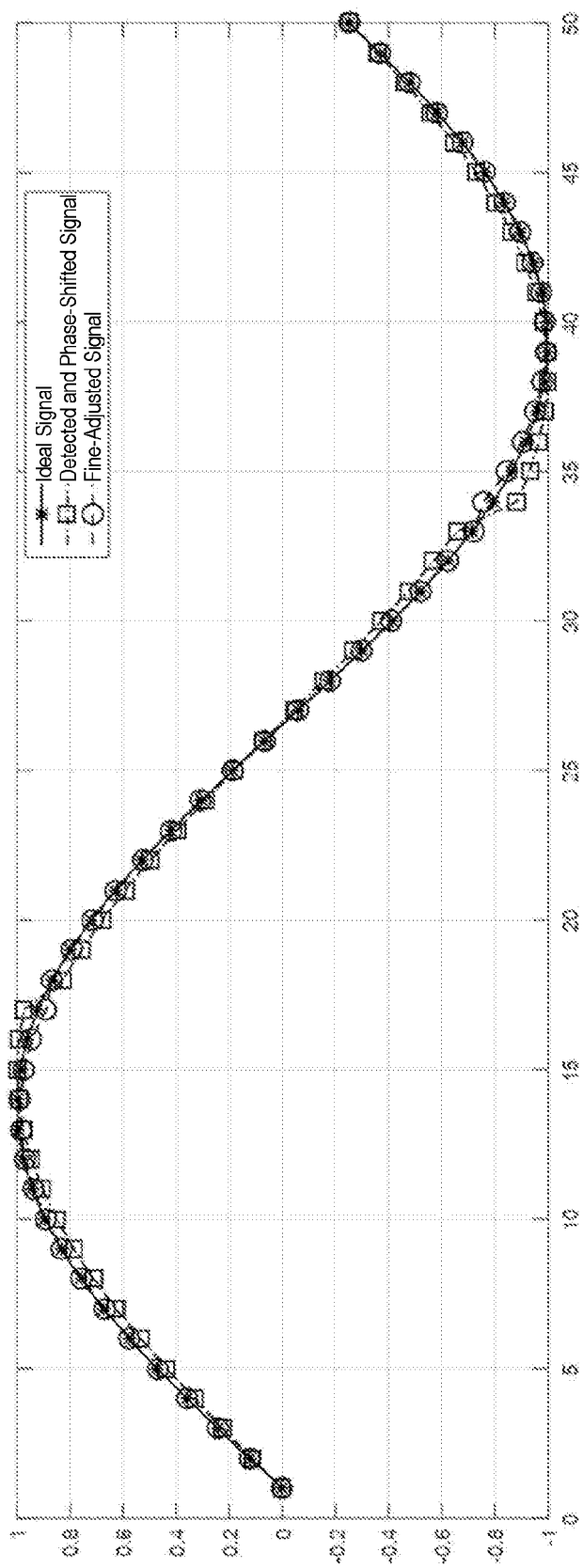
FIG. 7 is an example of a phase-shifted shear wave signal after fine-adjustment of the phase at each time point.

In some instances, such as when the choice of $f_s$ and $f_0$ does not make the minimization result of Eqn. (5) equal to zero, there may be a discrepancy between the detected shear wave phase and the ideal shear wave phase. In practice, this may happen, for example, when it is challenging to change $f_s$ to the exact optimal value derived from Eqn. (5). Also, there may be some instances where it may be inconvenient to change the shear wave frequency during scanning. When this happens, the detected shear wave signal may not exactly match the ideal shear wave signal because of the phase mismatch at each time point. To correct for this mismatch, the phase of the shear wave signal can be fine-adjusted at each time point using various methods, such as a Fourier transform-based or a Hilbert transform-based phase shifts. As shown in FIG. 7, after applying such fine-adjustment of the phase at each time point, a more accurate match to the ideal shear wave signal can be obtained. The amount of phase shift that is needed for the fine adjustment at each time point can be obtained from Eqn. (5).

Figure 8:
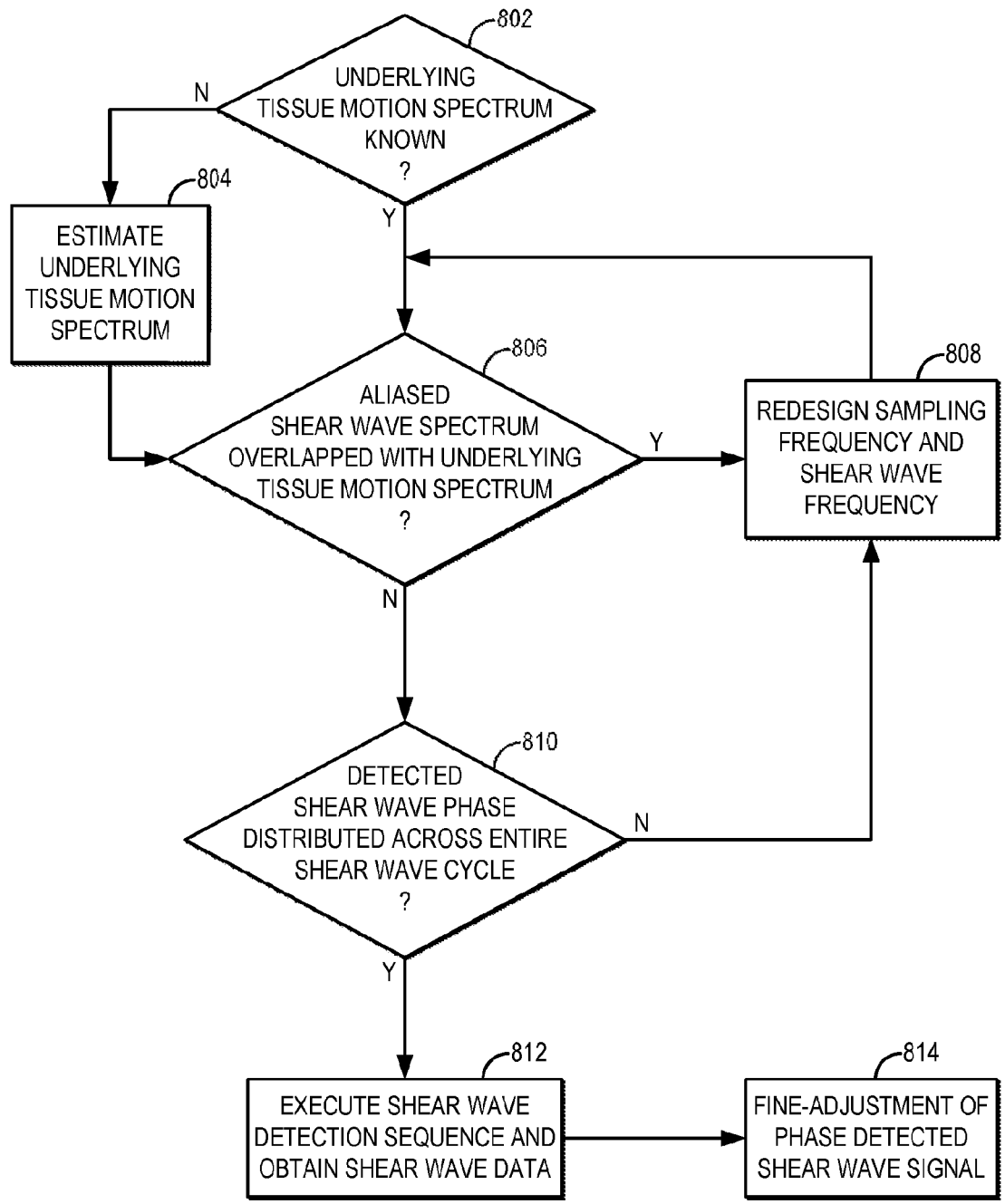
FIG. 8 is a flowchart setting forth the steps of an example method for correcting shear wave signal data for tissue motions.

Referring now to FIG. 8, a flowchart is illustrated as setting forth the steps of an example method for removing underlying tissue motion from harmonic shear wave signals using the methods described above. The method includes determining at step 802 whether the underlying tissue motion spectrum is known. If not, then the tissue motion spectrum is estimated, as indicated at step 804. As described above, this step can include empirically estimating or measuring the tissue motion. For instance, the tissue motion can be estimated by acquiring data from a subject while harmonic shear waves are not induced in the subject.

When the underlying tissue motion spectrum is known, or otherwise estimated, a determination is made at step 806 as to whether the aliased shear wave spectrum is overlapped with the underlying tissue spectrum. If so, then the sampling frequency, $f_s$, and shear wave frequency, $f_0$, are redesigned at step 808 to separate the two signals.

When the underlying tissue spectrum has been removed, a determination is made at step 810 as to whether the detected shear wave phase is distributed across the entire shear wave cycle. If not, then the sampling frequency, $f_s$, and shear wave frequency, $f_0$, are redesigned at step 808 to distribute the shear wave phase more uniformly across the entire shear wave cycle.

When the shear wave phase is distributed across the entire shear wave cycle, the designed shear wave detection sequence is executed by the ultrasound system to acquire shear wave data, as indicated at step 812. If desired, fine-adjustment of the phase of the detected shear wave signal can be applied, as indicated at step 814, and described above in more detail.

In another example method for removing underlying tissue motion from harmonic shear wave signals, a scanning sequence that may be referred to as a "snapshot" sequence can be used to remove the underlying tissue motion for harmonic shear wave detection.

In general, the snapshot scanning sequence includes repeating each subvolume scan twice before advancing to the next subvolume, as indicated below, $$\left\{\begin{matrix} V_{1,1} \to V_{1,1} \to V_{1,2} \to V_{1,2} \to \ldots \to V_{1,n} \to V_{1,n} \to V_{2,1} \to V_{2,1} \to \\ \ldots \to V_{2,n} \to V_{2,n} \to \ldots \to V_{m,1} \to V_{m,1} \to \ldots \to V_{m,n} \to V_{m,n} \end{matrix}\right\}_R$$

where this sequence is repeated R times. The time interval between the two repeated subvolume scans is selected to be sufficiently short (e.g., $1/f_{PRF}$) as compared to the frequency of the underlying tissue motion such that the underlying tissue motion can be assumed to be negligible between the two repeated scans. With this choice of time interval, it can be reasonably assumed that only shear wave propagation induced tissue motion is detected, analogous to taking a snapshot of the shear wave motion.

Figure 9:
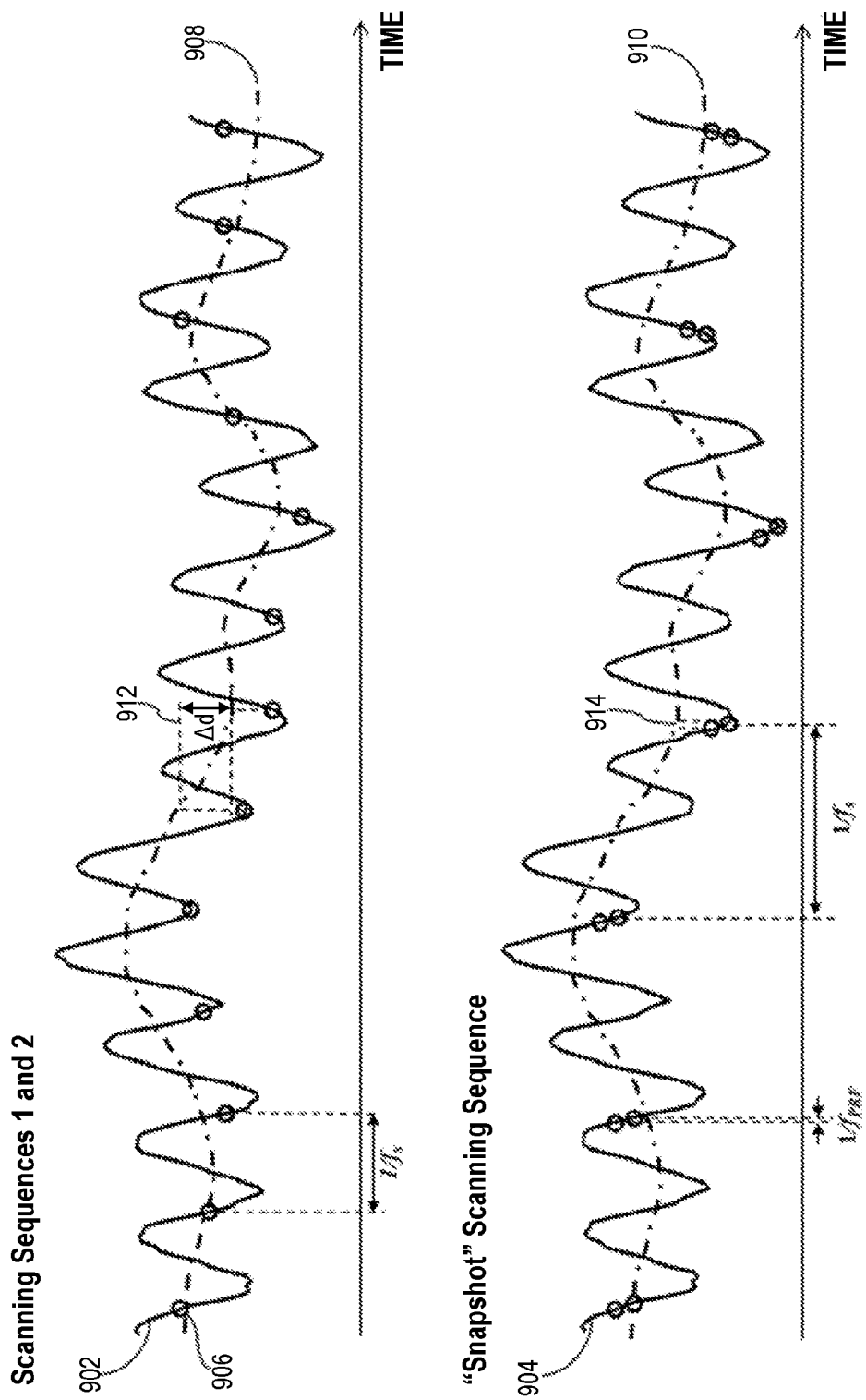
FIG. 9 illustrates an example of a snapshot scanning sequence compared to other scanning sequences for acquiring harmonic shear wave motion data.

The snapshot scanning sequence is further illustrated in FIG. 9. The signal plots 902 and 904 show the combined shear wave and underlying tissue motion, whereas signal plots 908 and 910 show the underlying tissue motion only. The hollow circles 906 indicate the temporal locations of the ultrasound data samples. For ultrasound shear wave motion calculations, a pair of ultrasound data samples (i.e., a pair of $V_{1,1}$ subvolume samples) is used to calculate the amount of tissue movement that occurred during the time interval between the pair of data samples.

For scanning sequences 1 and 2 described above, this time interval is $1/f_s$, and the shear wave motion is calculated by using consecutive pairs of data samples (e.g., sample 1 and sample 2, sample 2 and sample 3, sample 3 and sample 4).

For the snapshot scanning sequence, this time interval is $1/f_{PRF}$, or another sufficiently small time interval, which is typically much shorter than the time interval of $1/f_s$. Also, based on the snapshot scanning sequence, the shear wave motion can be calculated by using non-overlapping pairs of data samples (e.g., sample 1 and sample 2, sample 3 and sample 4, sample 5 and sample 6).

With scanning sequences 1 and 2, the amount of underlying tissue motion ($\Delta d$ indicated at 912) between two data samples is significant as compared to the shear wave motion.

In the snapshot scanning sequence, the underlying tissue motion between two data samples is negligible, as indicated at 914.

For the snapshot scanning sequence, because a pair of non-overlapped ultrasound data samples is used to calculate a shear wave motion signal at a time instant, the amount of total scanning time per frame or per volume is twice as long as that of the scanning sequences 1 and 2 described above. As a result, the shear wave sampling frequency $f_s$ for the snapshot sequence is given by, $$f_s = \frac{f_{PRF}}{2mn + t_c f_{PRF}}. \quad (6)$$

In this instance, the shear wave signal may still be aliased because the sampling frequency is even lower than that of scanning sequences 1 and 2. However, unlike in scanning sequences 1 and 2 where the aliased shear wave signal should be positioned so as not to overlap with the underlying tissue spectrum, in this snapshot scanning sequence the underlying tissue motion is minimal and can be neglected. Thus, the aliased shear wave signal can be easily recovered by using techniques such as the phase-shifting approach described in co-pending International Appln. No. PCT/US2016/055649.

Because of the longer scanning time per frame or volume for the snapshot scanning sequence, the amount of temporal shear wave samples per total allowed scanning time will typically be less than that of scanning sequences 1 and 2. Nevertheless, the minimization approach introduced in Eqn. (5) can be used to evenly distribute the detected shear wave samples across the entire shear wave cycle. Similarly, the fine-adjustment method described above can be used in the end to fine-adjust the phase of each shear wave sample to better match the ideal shear wave phase distribution.

Figure 10:
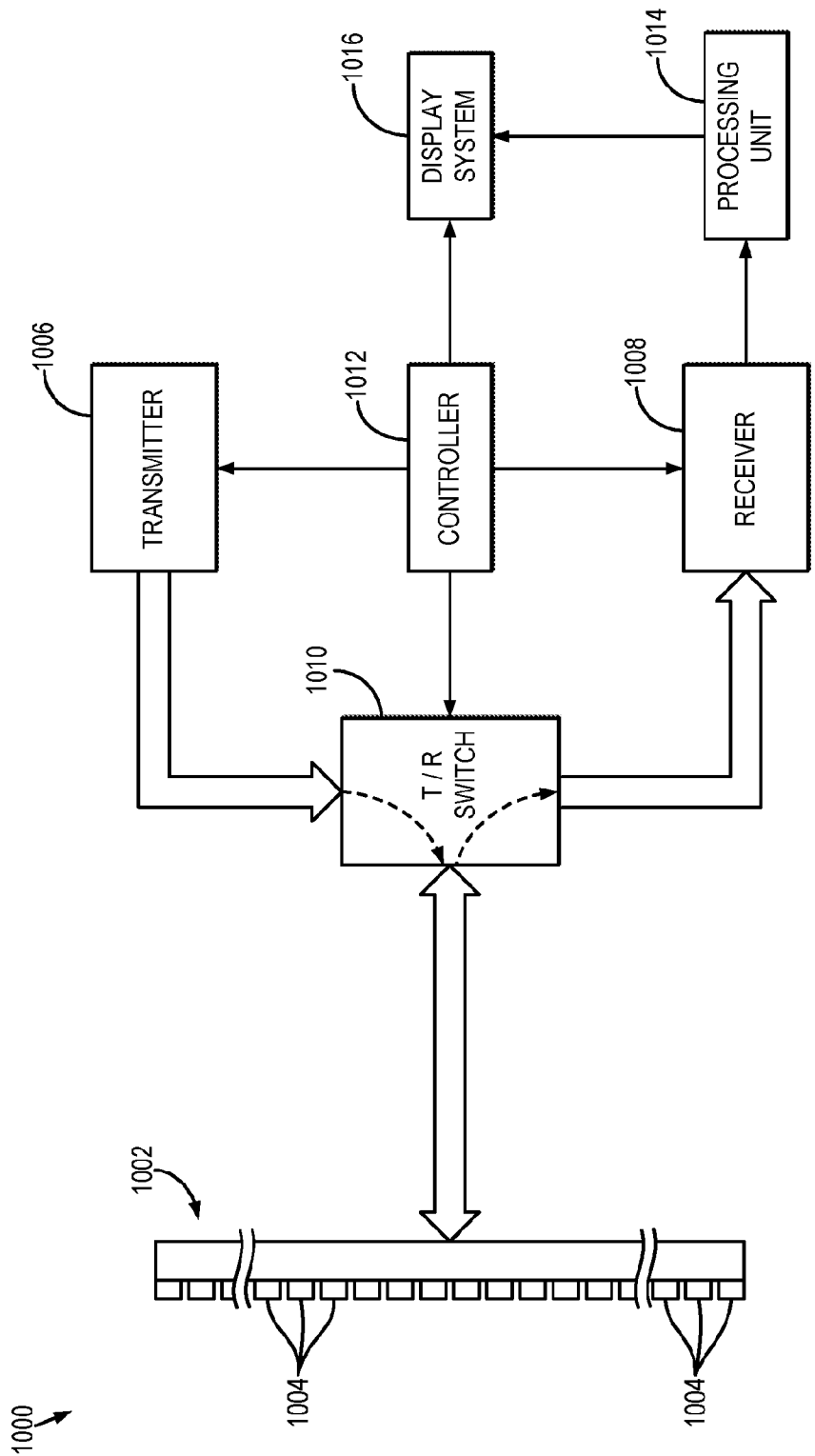
FIG. 10 is a block diagram of an example ultrasound system that can implement the methods described in the present disclosure.

FIG. 10 illustrates an example of an ultrasound system 1000 that can implement the methods described in the present disclosure. The ultrasound system 1000 includes a transducer array 1002 that includes a plurality of separately driven transducer elements 1004. The transducer array 1002 can include any suitable ultrasound transducer array, including linear arrays, curved arrays, phased arrays, and so on. Similarly, the transducer array 1002 can include a 1D transducer, a 1.5D transducer, a 1.75D transducer, a 2D transducer, a 3D transducer, and so on.

When energized by a transmitter 1006, a given transducer element 1004 produces a burst of ultrasonic energy. The ultrasonic energy reflected back to the transducer array 1002 (e.g., an echo) from the object or subject under study is converted to an electrical signal (e.g., an echo signal) by each transducer element 1004 and can be applied separately to a receiver 1008 through a set of switches 1010. The transmitter 1006, receiver 1008, and switches 1010 are operated under the control of a controller 1012, which may include one or more processors. As one example, the controller 1012 can include a computer system.

The transmitter 1006 can be programmed to transmit unfocused or focused ultrasound waves. In some configurations, the transmitter 1006 can also be programmed to transmit diverged waves, spherical waves, cylindrical waves, plane waves, or combinations thereof. Furthermore, the transmitter 1006 can be programmed to transmit spatially or temporally encoded pulses.

The receiver 1008 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 1006 and the receiver 1008 can be programmed to implement a high frame rate. For instance, a frame rate associated with an acquisition pulse repetition frequency ("PRF") of at least 100 Hz can be implemented. In some configurations, the ultrasound system 1000 can sample and store at least one hundred ensembles of echo signals in the temporal direction.

The controller 1012 can be programmed to design an scanning, or imaging, sequence using the techniques described in the present disclosure, or as otherwise known in the art. In some embodiments, the controller 1012 receives user inputs defining various factors used in the design of the imaging sequence.

A scan can be performed by setting the switches 1010 to their transmit position, thereby directing the transmitter 1006 to be turned on momentarily to energize transducer elements 1004 during a single transmission event according to the designed or otherwise selected scanning sequence. The switches 1010 can then be set to their receive position and the subsequent echo signals produced by the transducer elements 1004 in response to one or more detected echoes are measured and applied to the receiver 1008. The separate echo signals from the transducer elements 1004 can be combined in the receiver 1008 to produce a single echo signal.

The echo signals are communicated to a processing unit 1014, which may be implemented by a hardware processor and memory, to process echo signals or images generated from echo signals. As an example, the processing unit 1014 can produce images using the methods described in the present disclosure. Images produced from the echo signals by the processing unit 1014 can be displayed on a display system 1016.

The present disclosure has described one or more preferred embodiments, and it should be appreciated that many equivalents, alternatives, variations, and modifications, aside from those expressly stated, are possible and within the scope of the invention.

The invention claimed is:

1. A method for producing an image from shear wave data acquired from a subject using an ultrasound system, the steps of the method comprising:
   (a) providing an estimate of tissue motion in the subject to a computer system
   (b) generating a frequency spectrum of the estimate of the tissue motion
   (c) selecting a sampling frequency and a center frequency by spectrally analyzing the frequency spectrum of the estimate of the tissue motion in the subject, such that aliased shear wave signals are positioned in a frequency domain so as not to overlap with frequency bins corresponding to the tissue in the subject;
   (d) acquiring the shear wave data using the ultrasound system that is operated to acquire the shear wave data from the subject using the selected sampling frequency and center frequency while harmonic shear waves are induced in the subject;
   (e) generating filtered shear wave data by filtering the shear wave data to remove data corresponding to the tissue motion;
   (f) producing an image of the subject from the filtered shear wave data, wherein errors attributable to the tissue motion are reduced in the image.

2. The method as recited in claim 1, wherein the filtered shear wave data is generated by applying a highpass filter to the shear wave data.

3. The method as recited in claim 1, wherein the filtered shear wave data is generated by applying a bandpass filter to the shear wave data.

4. The method as recited in claim 1, wherein the estimate of the tissue motion is provided to the computer system by measuring the tissue motion in the subject with the ultrasound system without inducing harmonic shear waves in the subject.

5. The method as recited in claim 1, wherein selecting the sampling frequency and the center frequency includes selecting the sampling frequency and center frequency that minimize a cost function to evenly distribute phase of a detected shear wave signal from the acquired shear wave data across a full shear wave cycle.

6. The method as recited in claim 5, wherein the phase of the detected shear wave signal is adjusted using a fine-adjustment.

\* \* \* \* \*